(12) United States Patent
Sugita et al.

(10) Patent No.: US 6,319,225 B1
(45) Date of Patent: *Nov. 20, 2001

(54) INJECTION SYRINGE INCLUDING DEVICE FOR PREPARATION OF INJECTION

(75) Inventors: Koichi Sugita, Takarazuka; Sei Kirihara, Miki; Hiromichi Ishikawa, Kobe; Yutaka Igarashi, Sendai, all of (JP)

(73) Assignee: Nihon Chemical Research Co., Ltd., Ashiya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/266,916

(22) Filed: Mar. 12, 1999

(30) Foreign Application Priority Data

Mar. 19, 1998 (JP) .................................................. 10-092771

(51) Int. Cl.[7] .................................................. A61M 37/00
(52) U.S. Cl. .............................. 604/89; 604/82; 604/191
(58) Field of Search .................................. 604/82, 89, 90, 604/181, 187–188, 191, 200, 201, 205, 207, 212, 214, 218, 227, 232, 234–235, 240, 241, 244, 83, 84, 85, 88, 92, 258

(56) References Cited

U.S. PATENT DOCUMENTS

| 5,281,198 | * | 1/1994 | Hber et al. | 604/86 |
| 5,549,561 | * | 8/1996 | Hjertman | 604/131 |
| 5,569,191 | * | 10/1996 | Meyer | 604/82 |
| 5,630,800 | * | 5/1997 | Blank et al. | 604/82 |
| 5,807,323 | * | 9/1998 | Kriesel et al. | 604/89 |

* cited by examiner

Primary Examiner—Richard K. Seidel
Assistant Examiner—LoAn H. Thanh
(74) Attorney, Agent, or Firm—Oblon, Spivak, McClelland, Maier & Neustadt, P.C.

(57) ABSTRACT

An injection syringe including a device for preparation of an injection in situ, useful to the injection which is liable to suffer chemical changes if left for a long time in the state of solution or dispersion ready to inject. The injection syringe is portable by a patient who may prepare a necessary injection in situ with the use of a device included in the syringe which will automatically perform an injection with a prescribed dosage. The injection syringe includes a device for preparation of an injection, whereby mechanical impacts affecting the medicine and consequently, chemical changes with a medicine would be minimized during the step of dissolving the medicine. The syringe as noted is especially useful for preparation of injection and injection of human growth hormones, interferon and various polypeptides which are of an environmentally sensitive nature and liable to suffer chemical changes if left for a long time in the state of solution or dispersion.

10 Claims, 7 Drawing Sheets

INJECTION SYRINGE INCLUDING DEVICE FOR PREPARATION OF INJECTION

FIELD OF THE INVENTION

This invention relates to an injection syringe including a device for preparation of an injection in situ, useful to the injection which is liable to suffer chemical changes if left for long time in the state of solution or dispersion ready to inject. This invention particularly relates to an injection syringe portable by a patient who may prepare a necessary injection for himself in situ with use of a device included in the syringe which will automatically perform an injection with a prescribed dosage.

DESCRIPTION OF THE RELATED ART

Traditionally where a patient has to sit for injections regularly for a long period, for instance, injections of human growth hormones or insulin, such system has been employed as the patient always carries a kit of injection syringe and performs injections for himself. In this application in situ, an injection syringe is designed to be ready to be assembled by himself as well as to be suitable to multiple usage by exchange of ampules and needles. In this category, there has been known a portable syringe made up to be similar to a fountain pen.

On the other hand, in such application in situ as noted, some chemical substances including human growth hormones as well as interferon are subject to suffer unnegligible chemical changes only due to stirring or shake which may he occur in the process of dissolution or storage after the dissolution. Such environmentally sensitive substances are normally stored in ampules in the freeze-dried state, but careful treatment is required so that excessive mechanical force will not affect to such solution (or injecto. Plural form is "injections") during handling in dissolution or storage thereafter.

In view of such technical requirement as noted, in the case of an injection syringe including a multichambered cylindrical ampule which contains a solid medicine in a front space and a medicinal solvent in a rear space, and in the step of forwarding the rear gasket to let the solvent flow slowly into the front space en route of bypass, the known art has often employed the mechanism comprised of a manually turnable thread and a plunger connected with the rear gasket in order lo control a inflow rate. But complexity involved in such operations as well as stirring or shake with the syringe due to manual turning is unavoidable, and thus harmful affections to solutions or injections remain as task to be solved.

Further the front face of the space wherein a solid medicine was contained is sealed during the dissolution step and a remnant gas under compression remains at a tip of the space and then in the stop of injection or in the step of mounting an injection needle at the front tip of the space, as a result, the remnant gas will spout. Such action will exert an impact to the solution. Unfavorable consequence.

Heretofore such various systems have been proposed as will prepare injections with use of the multichambered ampule, but such systems heretofore admit of further improvement in the point of preventing possible stirring or disturbance to flow and other mechanical impacts affecting to the injections.

SUMMARY OF THE INVENTION

This invention is intended to offer an injection syringe in including a device for preparation of an injection, whereby mechanical impacts affecting to the medicine and consequently, chemical changes with a medicine would be minimized during the step of dissolving the medicine sealed in a space of the multichambered ampule and during the steps of storing and injecting the injection after the dissolution, and the injection syringe also including a device for dosage control as well as automatic injection, convenience to a patient who carries such injection syringe.

The target application of this invention lies in an injection syringe which will handle various polypeptides of environmentally sensitive nature including human growth hormones, interferon and which may be operated by a layman patient himself with readiness in situ.

The studies prove that a best suitable process for dissolution of an unstable freeze dried machine with a medicinal solvent is performed by manual control of the solvent flow with adequate slowness which will be monitored by eye observation on mixing conditions, and as for the injection step, it is proved that the dosage control will be optimized with use of an injection operator to be provided with syringe. In order for the syringe to be suitable for such requirements, a cylindrical ampule is sheathed or inset within a two-part case which will be retractable/extensibly by telescopic move between the two cases and which will be connected with an injection controllar or dosage controller. Thus dissolution will be performed with no working of the injection controllar which will work at the step of injection. Further, because the injection will possibly cause a back-flow due to the remnant gas as noted above, a reverse prevented mechanism may be optionally employed.

BRIEF DESCRIPTION OF THE DRAWINGS

FIG. 2($a$) shows another sectional view from the line A–A' of the same embodiment after the dissolution of the unstable freeze dried medicine is finished and a needle holder is mounted. FIG. 2($b$) shows a sectional view from the line B–B' in FIG. 1($a$).

FIG. 5($a$) shows a front view of a front case and a rear case. FIG. 5($b$) shows a sectional view from the line C–C' in FIG. 5($a$). FIGS. 6($a$) through 6($d$) are sectional views from the lines D–D', F–F', and G–G' in FIG. 5($a$) respectively.

FIGS. 7($a$) and ($b$) show two embodiments of combination between the rear gasket 11 and the plunger 19 in perspective view, wherein FIG. 7($a$) is for use in normal condition as shown in figures so far, and FIG. 7($b$) is for use with reinforcement against possible back pressure acting on the gasket 11, that is, a flange 17 is added to prevent deformation of the gasket 11.

DETAILED DESCRIPTION OF THE INVENTION

Figure 1A:
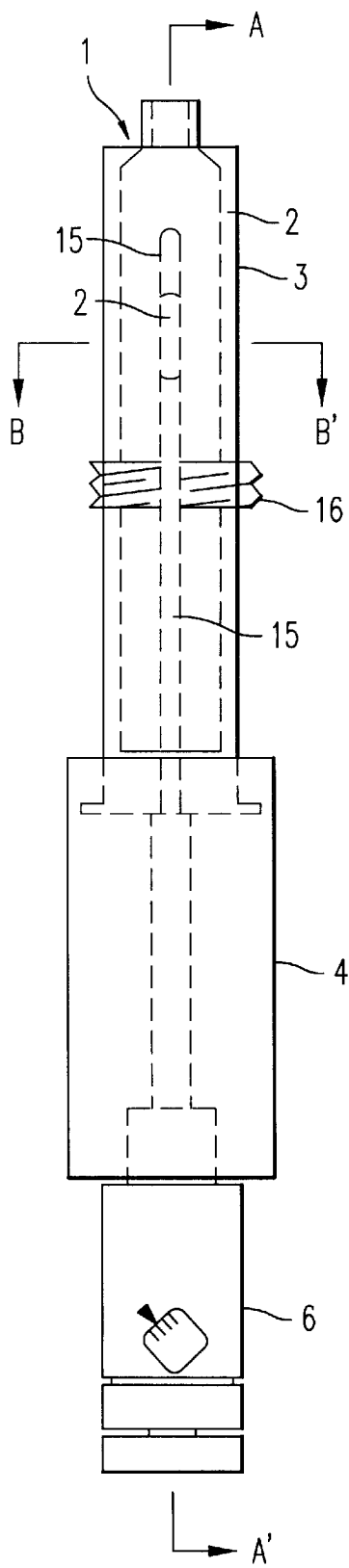
FIG. 1 shows an embodiment before the dissolution of an unstable freeze dried medicine, wherein a front view is shown by FIG. 1($a$), and a sectional view from line A–A' is shown by FIG. 1($b$).

An injection syringe 1 of this invention includes a device for preparation of an injection and is generally comprised of a multichambered cylindrical ampule 2, a front case 3, a rear case 4, a needle holder 5, injection controllar 6, and a plunger 19 as featured in (1), (2), (3) and (4) in the following:

(1) The multichambered cylindrical ampule 2 includes two chambers of a front space 7 and a rear space 8, the front space 7 being sealed forwardly with a packing 9 penetrable by a needle 28 and sealed rearwardly with a movable front gasket 10, and the rear space 8 being sealed forwardly with the front gasket 10 and sealed rearwardly with a movable rear gasket 11, and the ampule 2 also includes a bypass route 12 longitudinally arranged on inner surface of the ampule 2 such that the front gasket is located to take position rearwardly apart from the by pass route 12 before dissolution of an unstable freeze dried medicine 13 wherein the front space 7 for containing the unstable freeze dried medicine 13 is separated from the rear space 8 for containing a medical solvent 14 or dispersing agent 14.

(2) The front case 3 includes longitudinally on its inner surface a recess 15 for receiving the bypass route 12, and also includes a tapered tip portion to fix the front edge of the ampoule 2 inside thereof and a thread part 16 on its midportion to connect the rear case 4 after dissolution of the solid medicine, and a flange 17 at its rear edge.

(3) The rear case 4 includes a thread part 16' on its front portion and a mount part 18 on its rear portion such that the front case 3 is longitudinally inserted thereinto to provide movability with the flange 17 of the front case 3 between the thread part 16' and the mount part 18, and also includes at its rear end the connection to an injection controller 6 with inter mediation of the mount part 18 wherein the injection controller 6 is connected with the rear gasket 11 by a plunger 19.

(4) Wherein, in a process of dissolving the unstable freeze dried medicine 13 admitted in the front space 7 with the medicinal solvent 14 or dispersing agent 14 filled in the rear space 8, the injection controller 6 is forwardly moved manually, with no use of functions provided with the injection controller 6, such that the front gasket 10, the rear space 8 filled with the solvent 14, and the rear gasket 11 are moved forward in unison by the manual force acting on the plunger 19, and at the moment that the front gasket 10 enters into the bypass route 12's zone, the solvent 14 is released to flow into the bypass 12 to dissolve the unstable freeze dried medicine 13, and after all the solvent 14 has been sent off, the front and rear cases 3, 4 are tightened with working of two thread parts 16, 16', and thereafter the injection controller 6 is allowable to perform an injection, provided that the needle holder 5 is mounted on the packing 9, thus environmentally sensitive nature with the injection is overcome.

The invention further includes such modifications as providing a tubular stopper 20 between the rear end face of the ampule 2 and the inner face of the front case 3 for fastening together, and as providing a thread part 16", in place of the flange 17 of the front case 3, so as to mesh with a thread part 16' of the rear case 4.

The modification noted above continues to include such additions as providing two thread parts 23, 23" having cuts, on the mid- and rear-portions of the front case 21, to fix the rear case 22 such that a ratchet 24 is provided between the two thread parts 23, 23" for reverse detention, and as providing a thread part 23' having a cut, on the front portion of the rear case 22, such that the thread part 23' meshes to fix with the thread part 23" of the front case 21 before dissolution of the medicine, also providing a ratchet 24' on the midportion of the rear case 22 such the ratchet 24' meshes to fix with the ratchet 24 of the front case 21 for reverse detention.

Herein in this description, "solvent or dispersing agent" of "medicine" is meant to represent a liquid chemical to prepare an injection in either solution or emulsion form, though mostly such chemical is water, and the term "solution" or "solvent" sometimes includes "emulsion" or "dispersing agent" in this description.

Turning to the detailed description of the methodological aspect of this invention, the injection syringe of this invention is required to have suitability that a patient carries one set of the inventive syringe and he is convenienced to perform an injection for himself in situ, further required is suitability that a solid medicine may be dissolved in situ. It is because an unstable medicine chosen such as human growth hormones and thus the solution is unable to be stored for long period. Further required is immunity from the difficulty involved in the dissolution process wherein such unstable medicine is liable to suffer chemical changes due to mechanical forces such as stirring or shake affected during the dissolution.

A traditional syringe for the same application employs a multichambered ampule wherein a solid medicine and a medical solvent or dispersing agent are sealed in separate spaces and the patient is expected to operate the syringe for mixture or dissolution by himself. A task to be solved lies in how the solvent should be controlled so as to flow laminar state and to contact the solid medicine with minimum flow disturbance and minimum affection by mechanical force to the solid medicine.

The structure of the syringe of this invention designed to perform a process or manual handling of the syringe with methodological solution to such task, that is, the inventive structure expects such handling that the needle holder 5 is mounted before the dissolution at the front tip of the space containing the solid medicine in order to prevent a possible spout of remnant gas remaining at the.front tip space under compression, and that the dissolution process is performed by manual press onto the injection controller with no use of functions thereof. Herein said "the syringe is pressed without use of function of the injection controller" means specifically such manual operation as the syringe is set to be vertical on a desk or a some flat plane and then a downward press on the front case causes a relative upward move of the rear gasket while the injection controller is assigned to serve only as a base to hold the syringe. Further the syringe is provided with such structure as a longitudinal recess for receiving the bypass portion of the ampule is formed inside the front case wherein the ampule bypass portion which externally projects from the ampule surface is engaged into the recess and whereby free rotation of the ampule is prevented, thus stirring of the medicine is preferably prevented. However, this invention includes such a modification as dissolution is performed without the needle holder mounted at the front tip end, because such preparatory act is not always necessary to this invention.

Erecting and holding the syringe its front up is preferable in order for the liquid flow disturbance or other mechanical force to affect least to the medicine as well as the solvent in the dissolution process. For instance, erecting and holding the syringe to be vertical on a desk or flat plane, and soft manual pressing on the syringe downward with eye observation on actions inside the ampule, and whereby the plunger connected with the injection controller will act upwardly and slowly move the rear gasket of the ampule upwardly and then the solvent flows into the front space wherein the medicine is contained. Consequently attained is such inside performance that the solvent will flow through the bypass in laminar state and permeate the solid medicine slowly. The ampule has been inserted into the front and rear cases and the injection controller has been connected with intermediation of such cases, and in such dissolution process whereby, the longitudinal axis of the syringe will not flex to cause stirring with the solution. The syringe described so far is developed to attain the suitability to such handling in the dissolution process.

After the total volume of the solvent has been flown into the front space with regulation of its flow rate from the rear space under eye observation on the dissolution process of the medicine in the front space, tightening to set the thread part 16, 16' connecting the front and rear cases finishes the step of the dissolution process by the solvent. If the step proceeds to an injection step, a dosage amount is set on the injection controller and the rear end thereof is pressed.

In the inventive process wherein the syringe is pressed downwardly to move the rear gasket upwardly, so far as the space receiving the medicine is sealed, remnant gas collects at the tip end of the space under compression and such gas has a back pressure to cause a reversal flow as well as flow disturbance with the solvent. Therefore, it is preferable that the needle holder is mounted on the front edge of tile ampule before the dissolution process in order to avoid the stay of the remnant gas inside as well as to open a route for gas leak outside. However, the invention is feasible without the purge of the remnant gas, that is, it is allowable to store the injection containing the remnant gas under compression, depending on the quality of the syringe and the medicine. In this approach, it is preferable that the syringe is provided with ratchets interlocking the front and rear cases, See 5(a), 5(b) and 6(a) to 6(d). In this modification, the front and rear cases are meshed or interlocked during the solvent inflow from the rear space to the front space, sufficient to resist to a possible back pressure and to prevent the reverse flow, and effective to protect the medicine from possible quality change.

In use of the ratchet mechanism as noted above, vibrations causes by the ratchet are unavoidable. Therefore, it is preferable to use soft plastics or rubber as material of the ratchet mechanism to minimize such. On the other hand, the ratchet interlock may be released by turning the rear case about 90 degrees, and thus allowable is the solvent inflow under careful observation so as not to cause the unfavorable reverse phenomenon with no use of the ratchet interlock, and also allowable is reapplication of the interlock after the dissolution.

Figure 7B:
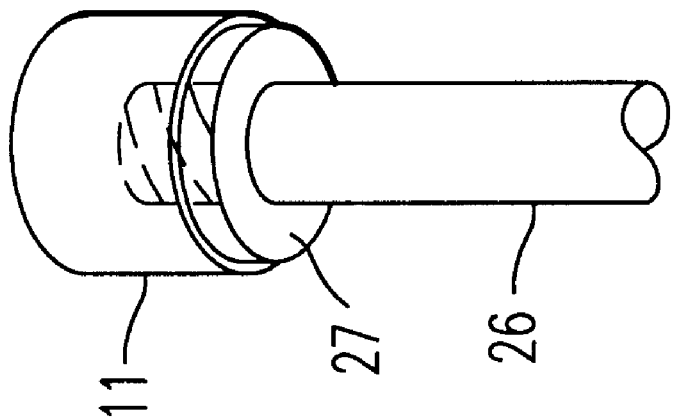
FIG. 7 includes two subfigures.
Figure 7A:
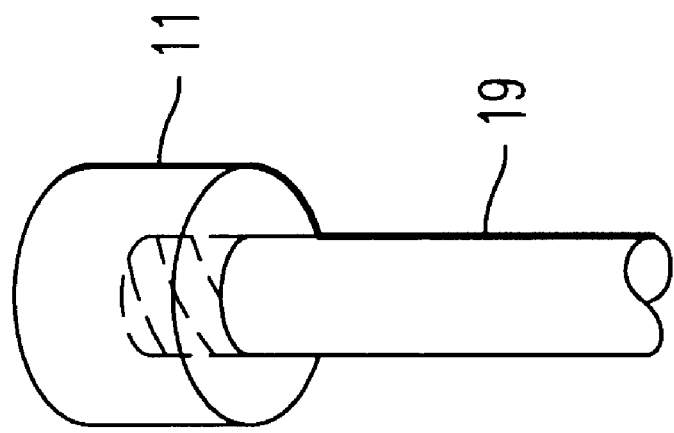

The connection between the plunger 19 and the rear gasket 11 may be made of a stud and recess coupling as shown in FIG. 7(a). In addition, the coupling may be improved by a flanged plunger end. The flange 27 is shown in FIG. 7(b). This modification is effective to avoid a deformation with the rear gasket 11, since a pressure large enough leading to the deformation will possibly act if the rear gasket is made from a flexible material such as rubber.

As for the injection controller or dosage controller, it is known that an apparatus for controlling a dosage amount by forwarding a plunger for a predetermined length, useful to perform an injection by a patient for himself. For instance, "AUTOPEN" brandnamed by Owen Mumford Ltd. is similar in appearance to a cap of a fountain pen which will inject a predetermined amount of an injection into the body based on setting of such amount after insertion of the needle into the body. As for dosage control, there are such systems as an element will forward with use of an urged spring based on a press on a button on the apparatus and as an element will forward with lead by finger press. This invention will accept any available systems so far as it can control a dosage amount predeterminable by operation acting on such apparatus. Further this invention will cover the use of such apparatus having functions similar to the notes above.

As for materials for constructing respective parts or elements constituting the syringe, there are no particular limitations, but plastics or rubbers are preferable in view of moldability. For the multichambered cylindrical ampule, preferable is glass, for the gasket, synthetic rubbers (nitrile rubber, silicon rubber, isoprene rubber, butadiene rubber, styrene-butadiene rubber, butyl rubber, chloroprene rubber, etc.), for the front and rear cases, AS resin(styrene acrylonitrile copolymer), acrylic resin, for the plunger, polypropylene. For the parts of the syringe, preferable are ABS resin (styrene acrylonitrile butadiene copolymer), polyethylene, polystyrene, polycarbonate, cycloolefin copolymer, polyethylene terephthalate, polyvinylchloride resin, metallic materials.

In the following, representative embodiments of the invention will be described with reference to the drawings.

EXAMPLE 1

Figure 1B:
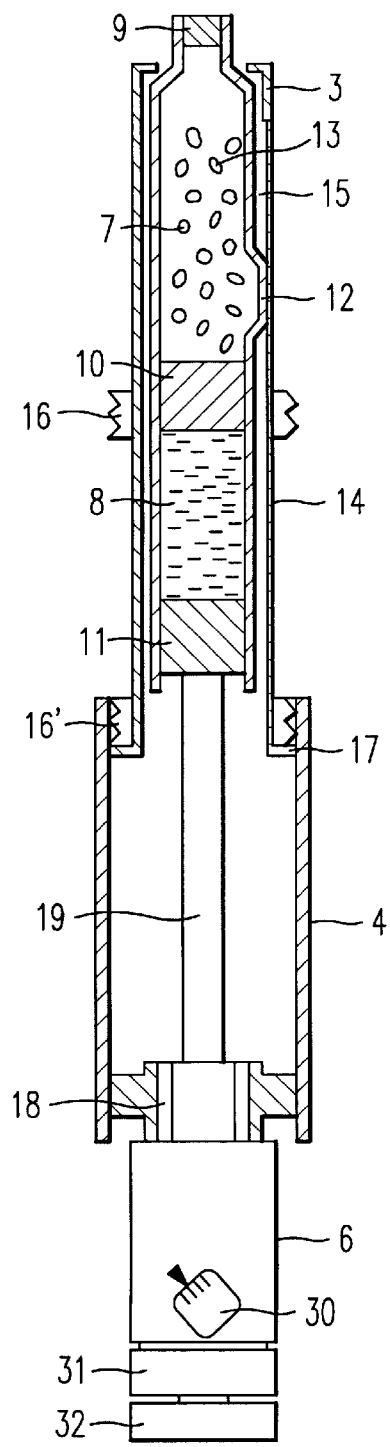
Figure 2A:
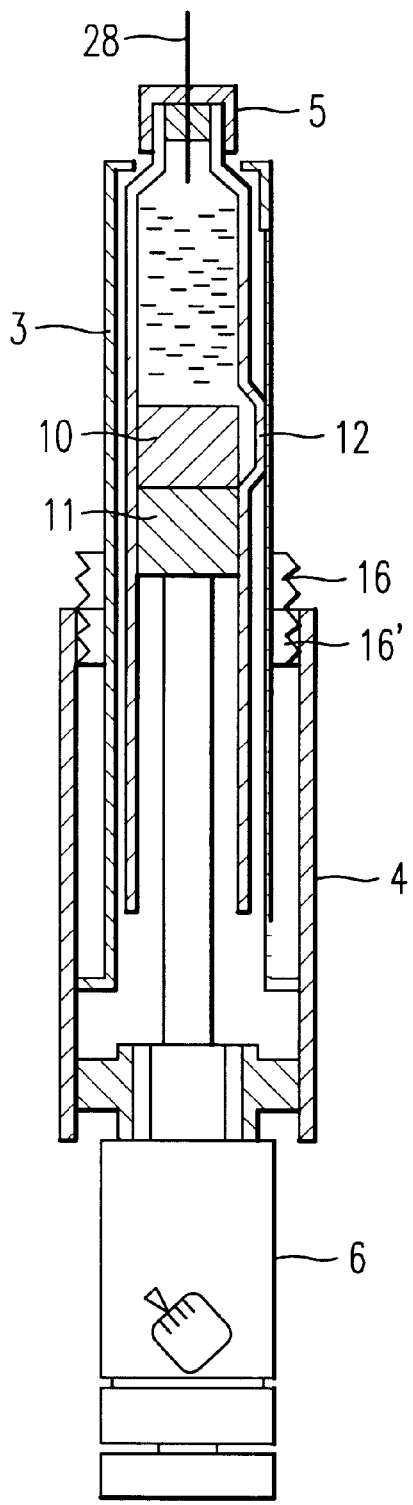
FIG. 2 includes two subfigures.
Figure 2B:
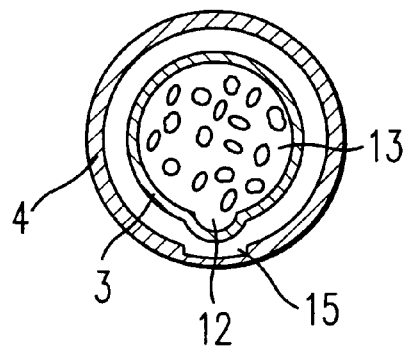

FIG. 1 shows an embodiment before the dissolution of a solid medicine, wherein a front view is shown by FIG. 1(a), and a sectional view from the line A–A' is shown by FIG. 1(b). FIG. 2(a) shows another sectional view from the line A–A' of the same embodiment after the dissolution of the unstable freeze dried medicine is finished and a needle holder is mounted. FIG. 2(b) shows a sectional view from the line B–B' in FIG. 1(a).

Referring to main materials of the syringe, a multichambered cylindrical ampule 2 is made from glass, gaskets are from synthetic rubber, a front case is from AS resin noted above, a rear case is from acrylic resin, a plunger is from polypropylene.

In a multichambered cylindrical ampule 2, a front space 7 is sealed forwardly with a packing 9 and rearwardly with a movable front gasket 10, and a rear space 8 is sealed forwardly with the front gasket 10 and rearwardly with a movable rear gasket 11. A longitudinal bypass route 12 is provided on a ampule wall projecting outwardly, wherein the front gasket 10 is located rearwardly apart from the bypass route 12, in other words, located clear of the bypass route 12 before the dissolution step, that is, an unstable freeze dried medicine 13 sealed in front space 7 is separated from a medicinal solvent 14 or dispersing agent 14 sealed in the rear space 8.

An ampule case includes two cylindrical cases; a front case 3 and a rear case 4 which are engaged concentrically with telescopic movability. The ampule 2 is inset or inserted into the front case 3, and inside thereof provided is a longitudinal recess 15 for receiving the bypass route 12 provided on the ampule 2. At midportion of the front case 3 a circumferential thread part 16 is outwardly provided, and a front tip end thereof is tapered to fix the ampule 2.

The rear case 4 is provided inwardly with circumferential thread part 16' at its front portion in order to match or mesh with the thread part 16 on the front case 3, and at its rear end, a mount part 18 acting like a stationary piston ring is fixed and is outwardly connected with an injection controller or dosage controller 6. The rear case 4 receives in its inside a circumferential flange 17 projected outwardly from the rear end of the front case 3 so that the thread part 16' will form abutment contact with the flange 17 not to let the same slip out forwardly from the rear case 4. In addition, possible rearward slip-out of the flange 17 is blocked by the mount part 18. Thus the flange 17 is slidable for length between the thread part 16' and the mount part 18, which is connected with a plunger 19 extending to the rear gasket 11.

In the Step of preparing a solution for injection or an injection, the injection controller 6 does not function to move the plunger 19. In this step, the injection syringe is erected on a desk or some plane and manual press on the syringe downwardly will cause the front and rear gasket 10, 11 to move forwardly (or upwardly) in unison with intermediation by plunger 19. At the moment the front gasket 10 enters into the bypass 12's zone, the solvent 14 filled in the rear space 8 starts flowing into the front space 7 whereby the unstable freeze dried medicine is dissolved. The dissolution finishes when the total solvent is flown thereinto. During the dissolution, the internal devices contained in the injection controller 6 are inactive and the injection controller 6 serves only as an anvil against the downward force.

After the total solvent 14 is transferred from the rear space 8 to the front space 7, two thread parts 16, 16' are tightened to fix the front and rear cases 3, 4, that is, the end of the dissolution step. In the step of injection, a dosage amount is set by a patient with looking at a dosage set dial 30 and by turning a nob 31, and whereby an injection controller end 32 is allowed to move in response to the amount set. It a needle of the syringe has been injected into the body and the operator end 32 is pushed toward the stop point, the prescribed amount of the injection will be injected into the body.

EXAMPLE 2

Figure 3A:
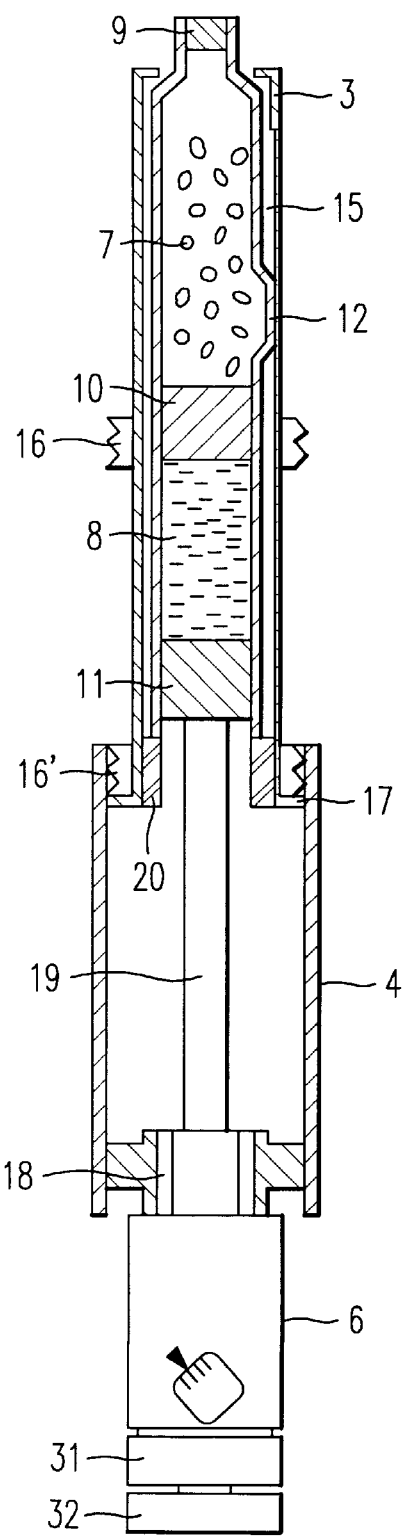
FIG. 3 shows another embodiment of the inventive injection syringe including a device for preparation of an injection, wherein FIG. 3($a$) shows a state before dissolution of the unstable freeze dried medicine and FIG. 3($b$) shows a state after the dissolution, both are views of longitudinal section.
Figure 3B:
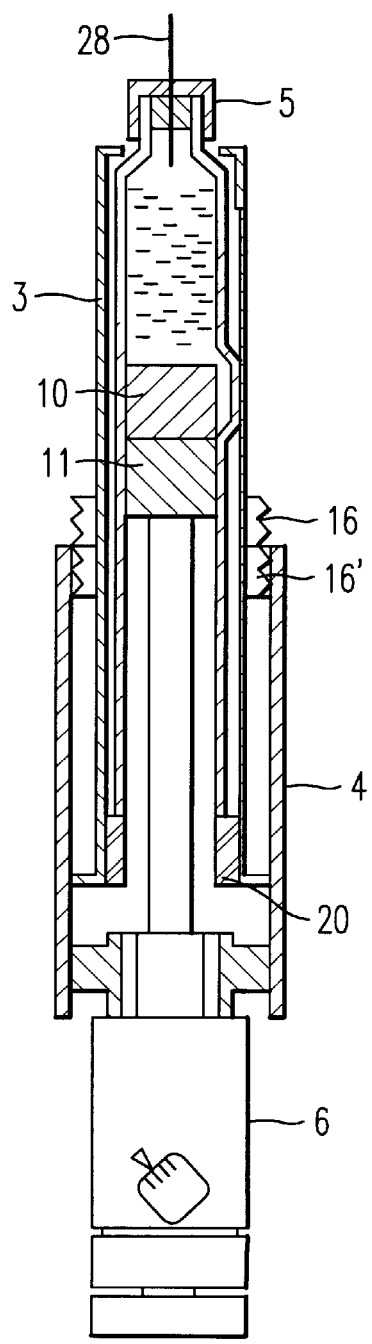

FIG. 3 shows another embodiment of the inventive injection syringe including a device for preparation of an injection wherein FIG. 3(a) shows a state before dissolution of the solid medicine and FIG. 3(b) shows a state after the dissolution, both are views of longitudinal section.

This embodiment features in the addition of a circumferential tubular stopper 20 inside the front case 3 after inset of the ampule 2 at a position to abut with the rear end face of the ampule 2 and also to fit the inner surface of the front case 3 at its rear end portion. The utility of this addition is explained in that the front edge of the ampule 2 is fixed by the tapering effect of the front case 3, and this addition complements fixation at the rear end of the ampule 2, and such is necessary when inserting the needle through the packing 9, since such operation exerts force downwardly. Otherwise, this embodiment is the same as noted above.

EXAMPLE 3

Figure 4A:
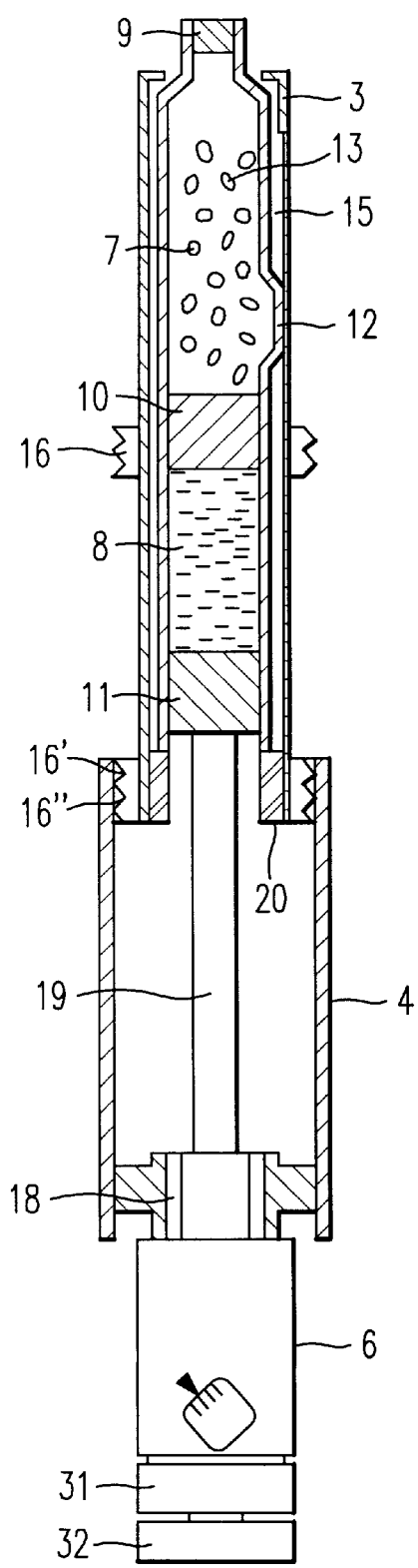
FIG. 4 shows another next embodiment of the inventive syringe including a device for preparation of an injection, wherein FIG. 4($a$) shows a state before dissolution of the unstable freeze dried medicine and FIG. 4($b$) shows a state after the dissolution, both are views of longitudinal section.
Figure 4B:
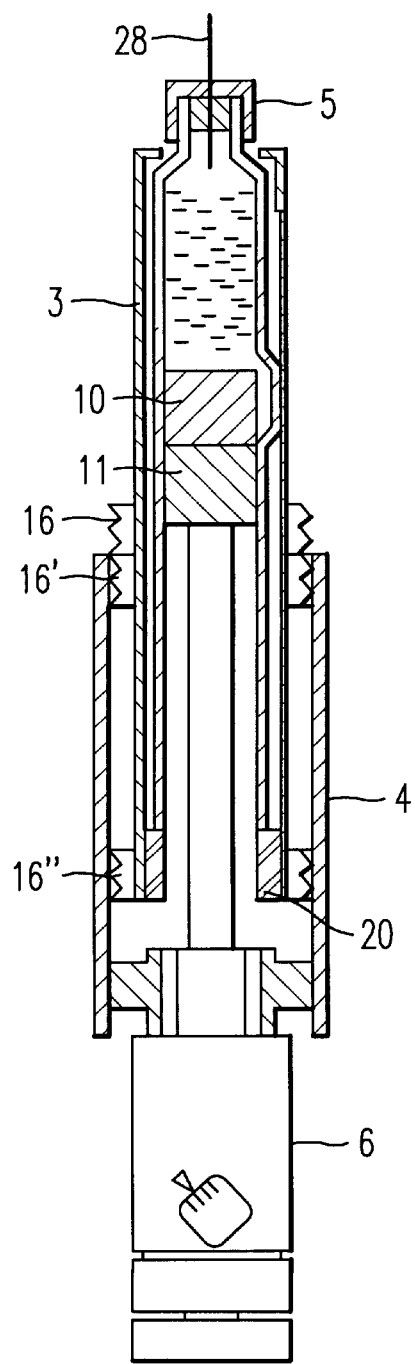

FIG. 4 shows another next embodiment of the inventive injection syringe including a device for preparation of an injection, wherein FIG. 4(a) shows a state before dissolution of the unstable freeze dried medicine and FIG. 4(b) shows a state after dissolution, both are views of longitudinal section.

This embodiment features in the addition of a circumferential thread part 16" in place of the flange 17 of the front case 3, that is, in this embodiment, the front case 3 is provided with a circumferential thread part 16" outwardly at its rear end to mesh with the thread part 16' provided inwardly at the front end of the rear case 4. This replacement is responsive to the need of improving productivity or ease in assembly work of inventive injection syringe, and the details thereof are abbreviated.

Based on the improvement noted above, the front case 3 provided with the thread part 16" noted above and the rear case 4 provided with the thread part 16' are fit longitudinally, and then the rear case 4 may advance further forwardly by way of entering into the meshing with 16' and letting the rear case 4 pass past the meshing with 16", that is, telescopic move in the engagement from a state shown in FIG. 4(a) to another state shown in FIG. 4(b).

Because the front case 3 and the rear case 4 are fastened each other with the thread part 16', 16", the ampule 2 is protected from external forces which will otherwise exert thereto and will possibly move the rear case 4 unexpectedly. Thus, the ampule 2 or the injection syringe 1 is stored safely.

EXAMPLE 4

Figure 5A:
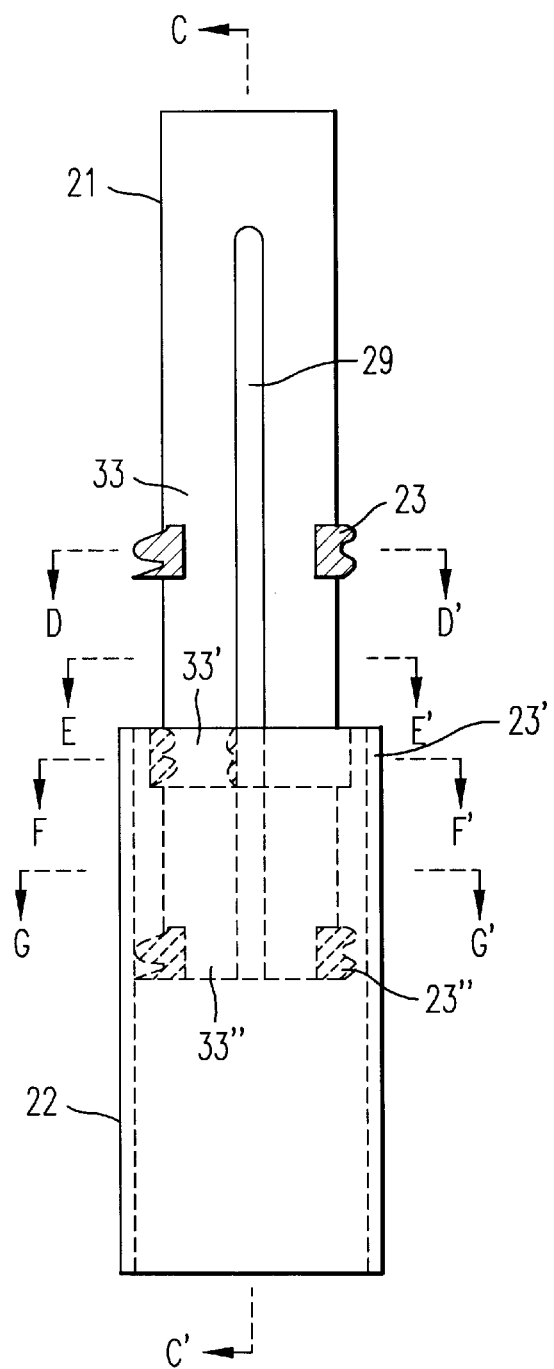
FIGS. 5 and 6 show partial views of embodiments belonging to the same inventive concept as disclosed so far, that is, parts unshown in these figures may be acceptable to assemble the whole embodiment by selecting any of the embodiments shown so far.
Figure 5B:
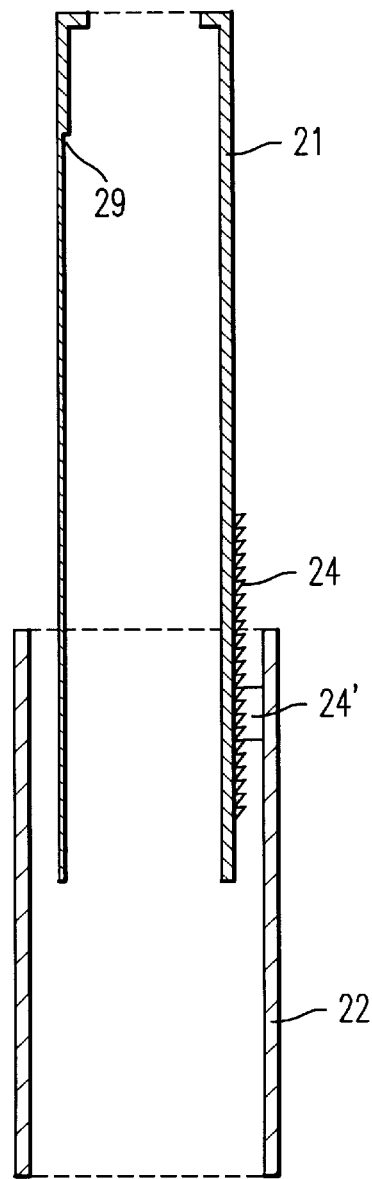

FIGS. 5 and 6 show partial views of embodiments belonging to the same inventive concept as disclosed so far, that is, parts unshown in these figures may be acceptable to assemble the whole embodiment by selecting any of the embodiments shown so far. FIG. 5(a) shows a front view of a front case and a rear case. FIG. 5(b) shows a sectional view from the line C–C' in FIG. 5(a). FIGS. 6(a) through 6(d) are sectional views from the lines D–D', E–E', F–F', and G–G' in FIG. 5(a) respectively.

Where the dissolution is performed without the needle holder 5 mounted on the packing 9, a reverse flow of the solvent 14 is possible from the front space 7 to the rear space 8 since the remnant gas is accumulated in the front space 3. What is shown in these figures is means for preventing such unfavorable phenomenon, that is, means for reverse detent. Herein, it is assumed that the front case 21 (formerly 3) is made from AS resin, and the rear case 22 (formerly 4) is from acrylic resin.

Figure 6A:
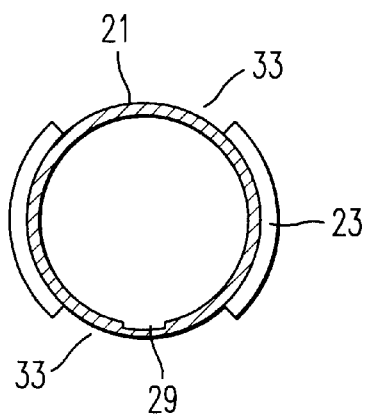
Figure 6B:
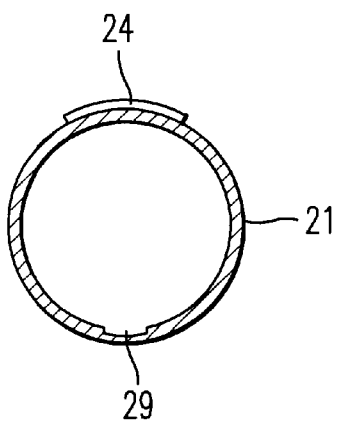
Figure 6C:
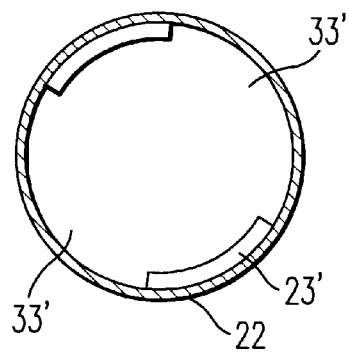
Figure 6D:
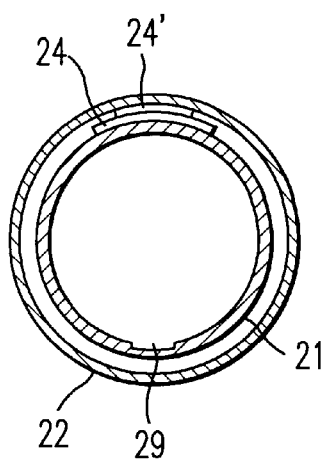

As is shown, a longitudinal recess 29 (formerly 15) for receiving a bypass route 12 is formed on the inner surface of the front case 21, and the front tip end of the front case 21 is tapered to fix the front edge of the ampule 2. At mid- and rear-portions of the front case 21, circumferential thread parts 23, 23" having partial cuts 33, 33" are mounted outwardly to fix the rear case 22 by meshing with a circumferential thread parts 23' having partial cuts 33', mounted inwardly on the inner surface of the rear case 22 wherein threads of these parts are designed to be common or the same in order to perform a precise meshing. FIG. 5(a) and FIG. 6(a) show cuts provided with these threads. Such cuts are useful to let the case 21 or 22 be free movable with no turning, that is, threads having cuts are useful to change movability conditions between the two cases 21, 22. And such free movability is obtained if the two cases are met under such condition that the two thread parts mounted on different cases are set to be staggered each other, whereby the front case 21 may readily move into the rear case 22.

The thread part 23' is mounted at the front end of the rear case 22 and is meshed with the thread part 23" on the front case 21 to fasten each other while being stored before the dissolution. Therein the threading art is so designed as to enter or to release the fastening by turning about 60 to 70 degrees in the crest meshed root state, (This situation may be understood by superposing FIG. 6(a) and FIG. 6(c). The superposed status will show disengagement or unfastening.)

and this fastening is effective to protect the ampule from being affected by external forces. As for the reverse detent, a longitudinal ratchet part 24 is mounted outwardly on a midportion of the front case 21 and a ratchet patch 24' is mounted inwardly on the rear case 22 to mesh with the ratchet 24.

In the step of the dissolution, as the rear gasket 11 relatively raises forwardly, ratchets 24, 24' mounted on the front and rear cases 21, 22 are put into action, that is, while the front case 21 lowers, the ratchets 24, 24' are meshed to prevent a reverse move, of which illustration is shown in FIG. 5(*b*) and FIG. 6(*d*). However, circumferential length of the ratchets 24, 21' is partial or not wide as shown in FIG. 6(*b*) and 6(*d*), and thus it is permitted to release the ratchet meshing and re-engage it, if such is thought to be necessary or more suitable. Operations after the dissolution step have been described above.

However, the use of the ratchet mechanism for reverse detent inevitably accompanies vibrations caused by the same mechanism. Thus preferable is the use of the ratchet devise made from flexible plastic or rubber. Otherwise, the dissolution is performed while the ratchet device 24, 24' is released by turning the rear case 22 about 90 degrees, and if the plunger 19 is stopped on the way, the ratchet device 24, 24' may be re-applied by re-turning the rear case 22. Such modification is permitted according to case by case judgement.

EXAMPLE 5

FIGS. 7(*a*) and (*b*) show two embodiments of combination between the rear gasket 11 and the plunger 26 in perspective view, wherein FIGS. 7(*a*) is for use in normal condition as shown in figures so far, and 7(*b*) is for use with reinforcement against possible back pressure acting on the gasket 11, that is, a flange 27 is added to prevent deformation with the gasket 11.

As noted before, the dissolution without the needle holder 5 mounted leads the remnant gas to accumulate and such pressure will act as back pressure against the inflowing solvent. The rear gasket 11 is normally made from rubber, material deformable due to such back pressure, and such pressure is possible to let the solvent leak through gap between the gasket periphery and the ampule wall. FIG. 7(*b*) is reinforcement to prevent such trouble, and is applicable to any embodiments shown so far.

What is claimed is:

1. An injection syringe for an unstable freeze dried medicine, including a device for preparation of an injection being generally comprised of a multichambered cylindrical ampule, a front case, a rear case, a needle holder, an injection controller, and a plunger:

(1) the multichambered cylindrical ampule including two chambers of a front space and a rear space, the front space being sealed forwardly with a packing penetrable by a needle and sealed rearwardly with a movable front gasket, and the rear space being sealed forwardly with the front gasket and sealed rearwardly with a movable rear gasket, and the ampule also including a bypass route longitudinally arranged on an inner surface of the ampule such that the front gasket is located rearwardly of the bypass route before dissolution of an unstable freeze dried medicine wherein the front space for containing said medicine is separated from the rear space for containing a medicinal solvent or dispersing agent;

(2) the front case including longitudinally on an inner surface thereof a recess for receiving the bypass route, and also including a tapered tip portion configured to fix the front edge of the ampule inside thereof and a thread part on a midportion thereof configured to connect the rear case after dissolution of the unstable freeze dried medicine, and a flange at a rear end thereof;

(3) the rear case including a thread part on a front portion thereof and a mount part on a rear portion thereof such that the front case is longitudinally inserted thereinto to provide movability with the flange of the front case between the thread part and the mount part, and also including at a rear flange end the connection to an injection controller with intermediation of the mount part wherein the injection controller is connected with the rear gasket by a plunger;

(4) wherein, in a process of dissolving the unstable freeze dried medicine admitted in the front space with the medicinal solvent or dispersing agent filled in the rear space, the injection controller is forwardly moved manually, with no use of functions provided with the injection controller, such that the front gasket, the rear space filled with the solvent, and the rear gasket are moved forward in unison by the manual force acting on the plunger, and at the moment that the front gasket enters into the bypass route zone, the solvent is released to flow into the bypass to dissolve the unstable freeze dried medicine, and after all the solvent has been sent off, the front and rear cases are tightened with working of two thread parts, and thereafter the injection controller is allowable to perform an injection, provided that the needle holder is mounted on the packing, thus environmentally sensitive nature with the injection is overcome.

2. An injection syringe including a device for preparation of an injection as noted in claim 1, wherein the plunger connected with the injection controller is provided with a plunger flange.

3. In a process for preparation of an injection with use of an injection syringe, said syringe, including a multichambered cylindrical ampule, a front case, a rear case, a needle holder, an injection controller, and a plunger, said multichambered cylindrical ampule including two chambers of a front space and a rear space, the front space being sealed forwardly with a packing penetrable by a needle and sealed rearwardly with a movable front gasket, and the rear space being sealed forwardly with the front gasket and sealed rearwardly with a movable rear gasket, and the ampule also including a bypass route longitudinally arranged on inner surface of the ampule such that the front gasket is located to take a position rearwardly apart from the bypass route before dissolution of an unstable freeze dried medicine, and wherein the ampule is set inside the front case and the rear gasket is connected with the injection controller by the plunger;

said process comprising the step of; containing the unstable freeze dried medicine into the front space and filling the rear space with a medicinal solvent or dispersing agent; erecting the injection syringe thus prepared in a front-up and rear-down status; pressing manually the injection syringe downwardly onto a base with no use of working by the injection controller such that the front and rear gaskets move upwardly by the force acting on the plunger and at the moment that the front gasket enters into the bypass route zone, the solvent filled in the rear space flows into the bypass route to dissolve the unstable freeze dried medicine in the front space wherein a flow rate is monitored and controlled manually by observation of a dissolving condition of said medicine, maintained in a laminar flow state so as not to cause stirring and shaking during the dissolution; tighten by meshing thread parts connecting the front and rear cases after all the solvent has been sent off the rear space.

4. An injection syringe for an unstable medicine, said injection syringe comprising:

an ampule including a unitary body having a first chamber adapted to contain an unstable medicine and a second chamber adapted to contain a medicinal solvent or dispersing agent, said first chamber being sealed forwardly with a packing and sealed rearwardly with a movable front gasket, said second chamber being sealed forwardly with said front gasket and sealed rearwardly with a movable rear gasket, said ampule having a bypass route longitudinally arranged on an inner surface of said ampule wherein said front gasket is located rearwardly of said bypass route before dissolution of the unstable medicine such that said first chamber is separated from said second chamber and wherein said front gasket is located at said bypass route after dissolution of the unstable medicine such that said first chamber is connected to said second chamber by said bypass route;

a first case including an inner surface having a recess configured to receive said bypass route, said first case including a tip portion configured to receive a front edge of said ampule inside thereof, said first case having a thread part, said first case having a flange on a rear end thereof, a second case including a thread part on a front portion configured to engage said thread part on said first case after dissolution of the unstable medicine thereof, said second case including a mount part on a rear portion thereof such that said first case is longitudinally inserted thereinto to provide movability with said flange of said first case between said thread part and said mount part; and an actuator connected to said rear gasket.

5. The injection syringe according to claim 4, further comprising an injection controller connected to said rear gasket by said actuator, wherein said rear case includes at a rear flange end a connection to said injection controller with intermediation of said mount part.

6. The injection syringe according to claim 5, wherein said actuator connected with said injection controller is provided with a plunger flange.

7. An injection syringe for an unstable medicine, said injection syringe comprising:

an ampule including a unitary body having a first chamber adapted to contain an unstable medicine and a second chamber adapted to contain a medicinal solvent or dispersing agent, said first chamber being sealed forwardly with a packing and sealed rearwardly with a movable front gasket, said second chamber being sealed forwardly with said front gasket and sealed rearwardly with a movable rear gasket, said ampule having a bypass route longitudinally arranged on an inner surface of said ampule wherein said front gasket is located rearwardly of said bypass route before dissolution of the unstable medicine such that said first chamber is separated from said second chamber and wherein said front gasket is located at said bypass route after dissolution of the unstable medicine such that said first chamber is connected to said second chamber by said bypass route;

a first case including an inner surface having a recess configured to receive said bypass route, said first case including a tip portion configured to receive a front edge of said ampule inside thereof, said first case having a flange on a rear end thereof;

a second case including a mount part on a rear portion thereof such that said first case is longitudinally inserted thereinto to provide movability with said flange of said first case within said second case;

an actuator connected to said rear gasket; and means for connecting said second case to said first case after dissolution of the unstable medicine such that a laminar flow state is maintained throughout the dissolution of the unstable medicine.

8. The injection syringe according to claim 7, further comprising an injection controller connected to said rear gasket by said actuator, wherein said rear case includes at a rear flange end a connection to said injection controller with intermediation of said mount part.

9. The injection syringe according to claim 8, wherein said actuator connected with said injection controller is provided with a plunger flange.

10. A process for preparing an injection using an injection syringe, the injection syringe including an ampule having a unitary body with a front chamber and a rear chamber, the front chamber being sealed forwardly with a packing and sealed rearwardly with a movable front gasket, the rear chamber being sealed forwardly with the front gasket and sealed rearwardly with a movable rear gasket, the ampule having a bypass route longitudinally arranged on an inner surface of the ampule, the injection syringe further including a front case configured to receive the ampule therein and having a thread part, a rear case having a thread part on a front portion, and an injection controller connected to the rear gasket by a plunger, said process comprising the steps of:

containing an unstable freeze dried medicine in the front chamber;

filling the rear chamber with a medicinal solvent or dispersing agent wherein the front gasket is located rearwardly of the bypass route before dissolution of the unstable medicine such that the front chamber is separated from the rear chamber;

orienting the injection syringe in a front-up and rear-down status;

pressing the injection syringe manually downward onto a base without use of the injection controller such that the front and rear gaskets move upwardly by force acting on the plunger wherein the front gasket is located at the bypass route such that the front chamber is connected to the rear chamber by the bypass route whereby the unstable medicine is dissolved;

controlling a flow rate through the bypass route in order to maintain a laminar flow state so as not to cause stirring and shaking during dissolution; and meshing the thread parts of the front case and the rear case after dissolution of the unstable medicine.

\* \* \* \* \*